United States Patent [19]

Hedberg

[11] Patent Number: 5,376,105

[45] Date of Patent: Dec. 27, 1994

[54] DEFIBRILLATOR/CARDIOVERTER

[75] Inventor: Sven-Erik Hedberg, Kungsaengen, Sweden

[73] Assignee: Siemens Aktiengesellschaft, Munich, Germany

[21] Appl. No.: 67,952

[22] Filed: May 27, 1993

[30] Foreign Application Priority Data

Jun. 17, 1992 [EP] European Pat. Off. ......... 92110294.3

[51] Int. Cl.$^5$ .............................................. A61N 1/00
[52] U.S. Cl. ................................................. 607/5
[58] Field of Search ........................................ 607/5-8

[56] References Cited

U.S. PATENT DOCUMENTS

| | | |
|---|---|---|
| 4,548,203 | 10/1985 | Tacker, Jr. et al. . |
| 4,708,145 | 11/1987 | Tacker, Jr. et al. . |
| 4,969,463 | 11/1990 | Dahl et al. . |
| 5,042,497 | 8/1991 | Shapland ............... 607/6 |
| 5,107,834 | 4/1992 | Ideker et al. . |
| 5,179,946 | 1/1993 | Weiss ..................... 607/6 |
| 5,188,105 | 2/1993 | Keimel ................... 607/5 |
| 5,190,034 | 3/1993 | Sholder ................... 607/5 |

FOREIGN PATENT DOCUMENTS

| | | | |
|---|---|---|---|
| 0280526 | 8/1988 | European Pat. Off. | ......... 607/5 |
| 0445800 | 9/1991 | European Pat. Off. . | |
| 0457604 | 11/1991 | European Pat. Off. . | |
| 0480569 | 4/1992 | European Pat. Off. . | |
| 3236756 | 4/1984 | Germany . | |
| 3919498 | 1/1990 | Germany . | |
| 888580 | 1/1962 | United Kingdom . | |
| 2018198 | 10/1992 | WIPO | ......... 607/5 |

Primary Examiner—William E. Kamm
Assistant Examiner—Marianne H. Parker
Attorney, Agent, or Firm—Hill, Steadman & Simpson

[57] ABSTRACT

In order to be able to set a current distribution in the heart in the event of defibrillation which is optimum both spatially and temporally, a pulse-generating device is provided having n-1 outputs connected in series, to which a total of n output terminals and n electrodes are connected. The device generates output pulses at its outputs which temporally overlap one another at different times and in different numbers.

10 Claims, 3 Drawing Sheets

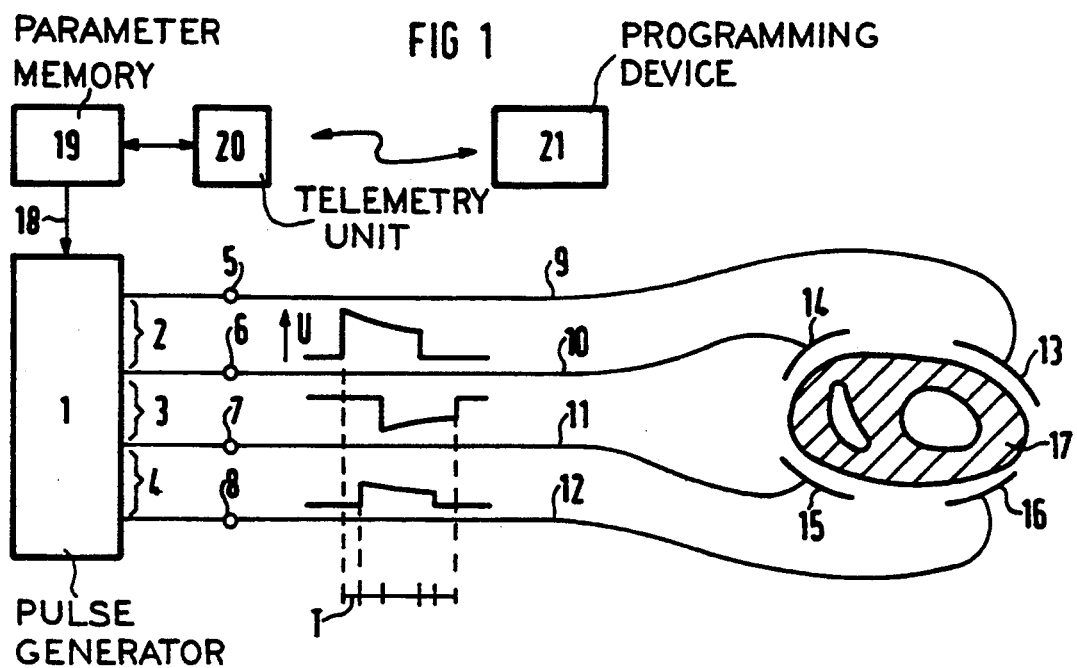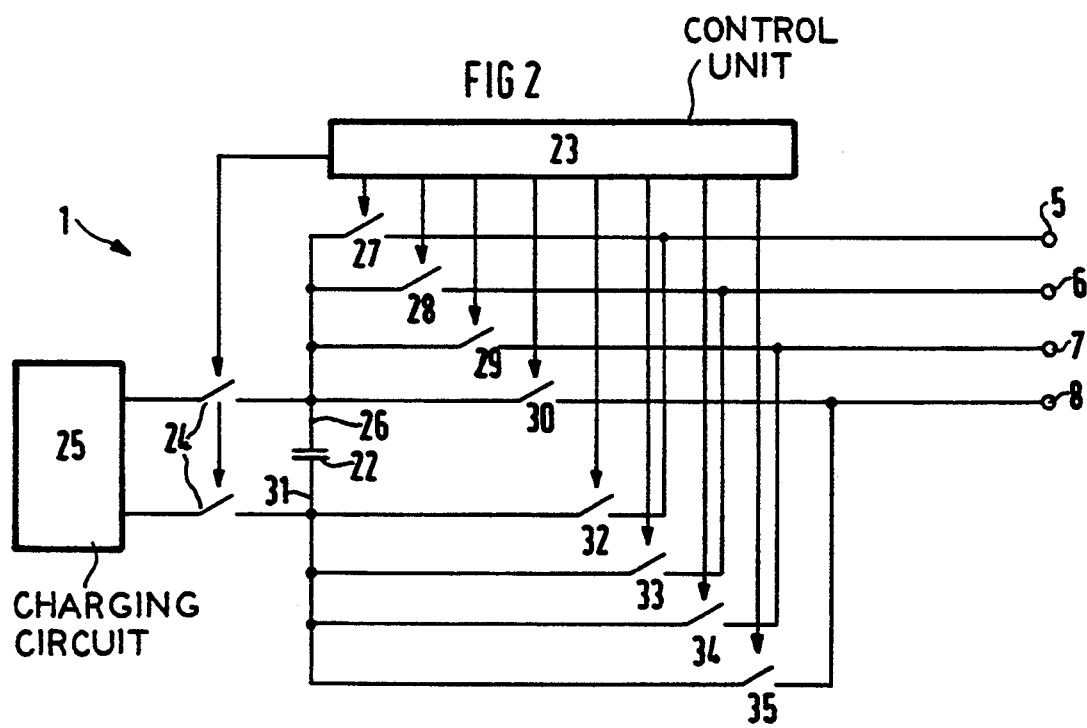

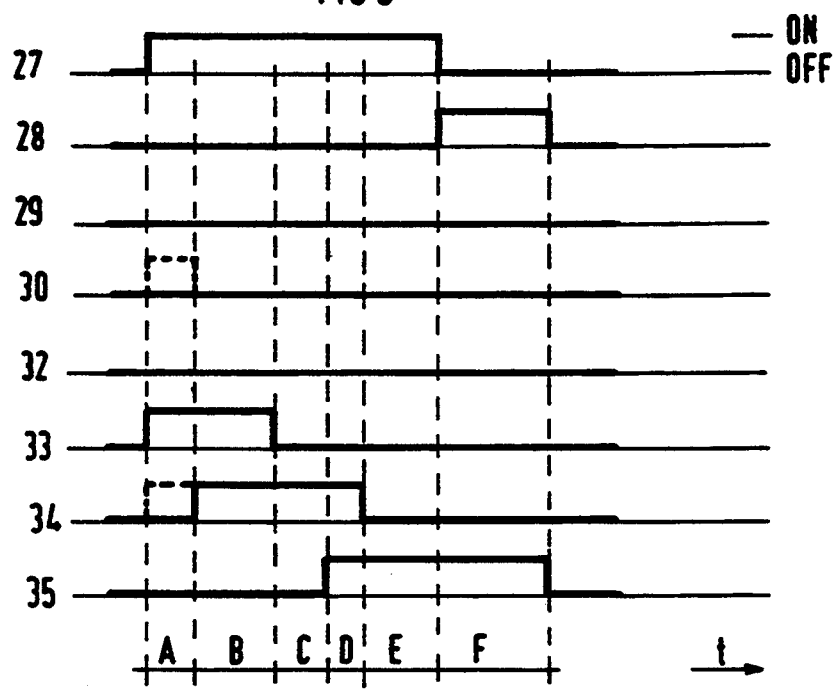
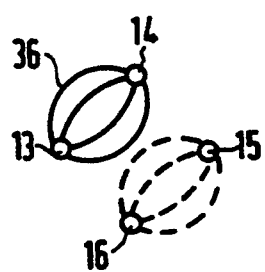
FIG 4a
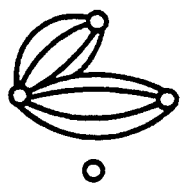
FIG 4b
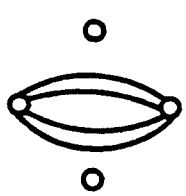
FIG 4c
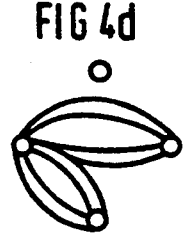
FIG 4d
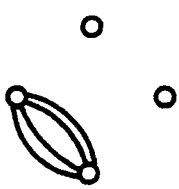
FIG 4e
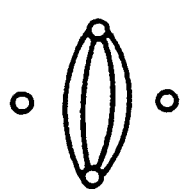
FIG 4f

DEFIBRILLATOR/CARDIOVERTER

BACKGROUND OF THE INVENTION

1. Field of the Invention

The present invention relates to a defibrillator/cardioverter of the type having a plurality of n (n>3) electrodes which are connected to a device for generating electric pulses.

2. Description of the Prior Art

A defibrillator or cardioverter is disclosed in German OS 3,919,498, wherein one of a plurality of electrodes is arranged in the interior of the heart and the remaining electrodes are placed outside of the heart. The external electrodes are electrically connected to one another and are connected to a first of two output terminals of a pulse generator. The electrode arranged in the interior of the heart is connected to the second output terminal. It is thereby achieved that, upon the transmission of an electrical pulse by the pulse generator, the electrical current density is distributed in the heart muscle in accordance with the arrangement of the electrodes and preferably penetrates the thickest zones of the heart muscle, which form the main part of the heart muscle mass, in order to achieve defibrillation or cardioversion. The current distribution, however, can be set only by the arrangement and size of the individual electrodes. The arrangement of the electrodes, and in particular their distance from one another, is limited, however, by the anatomical conditions.

U.S. Pat. No. 4,548,203 discloses a further defibrillator having a plurality of electrodes which are connected in pairs to different outputs of a pulse generator and are placed on different, preferably opposite, sites of the heart. In order to defibrillate the heart, one electric pulse is applied to the individual electrode pairs sequentially via the outputs of the pulse generator, the pulses being separated from one another in each case by a time interval. The spatially and temporally separate pulse transmission is intended to achieve a reduction in the energy required to trigger the defibrillation. In each case, however, only two electrodes simultaneously participate in the pulse transmission, and thus a genuine distribution of the current density to different zones of the heart muscle is difficult to achieve if at all.

In a further defibrillator, disclosed in U.S. Pat. No. 4,708,145, having three electrodes, transmission of defibrillation pulses is performed sequentially between a first electrode and in each case one of the other two electrodes, the pulses again being separated from one another by a time interval.

European Application No. 92104392.3 (corresponding to pending U.S. application Ser. No. 07/856,688, filed Mar. 24, 1992, Hirschberg et al., "Defibrillator/Cardioverter"), discloses an arrangement which achieves a spatially optimum current distribution when the individual electrodes are connected to respective output terminals, which are in turn connected to a plurality of series-connected outputs of a pulse generator which simultaneously transmits an electric pulse at each of those outputs.

SUMMARY OF THE INVENTION

It is an object of the present invention to provide a defibrillator or cardioverter by means of which it is possible to set a both spatially and temporally optimum current distribution in the heart in order to achieve defibrillation which is as effective as possible.

The above object is achieved in accordance with the principles of the present invention in a defibrillator/cardioverter having a pulse generator with n-1 series-connected outputs with a total of n output terminals to which the electrodes are connected, and wherein the pulse generator transmits, at each of its outputs, one electric output pulse, with a different number m (1>m>n-1) of the output pulses being transmitted in directly successive time intervals so that the pulses overlap in different combinations. It is thereby achieved that the electric current fed to the heart via the electrodes during the defibrillation penetrates different regions of the heart with different current densities in the successive time intervals, so that the different regions of the heart are sequentially defibrillated and a resurgence of defibrillation is prevented. Due to the pulse transmission, performed in a temporally overlapping fashion, at the different outputs of the pulse-generating device, it is possible, moreover, to create bi-phasal current characteristics in prescribed regions of the heart which have proved particularly effective for defibrillation purposes.

In order to be able to apply different current densities sequentially to the different regions of the heart, the pulse generator includes means for generating the output pulses with respective different pulse starting times, pulse duration and/or pulse height.

A particularly simple construction of the defibrillator/cardioverter according to the invention is achieved in an embodiment wherein the pulse generator has a capacitor which can be connected for recharging to a charging circuit, the capacitor being connected on one side via controllable switches to each one of the output terminals of the device. The capacitor is likewise connected on its other side via further controllable switches to each of the output terminals, and a control device is provided for individually turning the switches on and off. It is thus possible to connect different electrodes in different numbers to the respective two sides of the capacitor at different instances, and thereby to achieve a desired characteristic of the current distribution in the heart.

In a further embodiment of the defibrillator/cardioverter according to the invention, pulse generator has n-1 series-connected capacitors which can be connected for recharging to a charging circuit, the terminals of the individual capacitors being connected via individually controllable switches to the output terminals of the device, and a control device being provided for individually turning the individual switches on and off. As a result, a further variation in the current distribution in the heart is rendered possible during defibrillation, because the pulse heights of the pulses fed in an overlapping fashion to the heart can be set by recharging the capacitors to different charging voltages. This can be performed in the simplest case by recharging the series circuit composed of the capacitors to a charging voltage prescribed by the charging circuit, the ratio of the component voltages across the individual capacitors depending on their capacitance.

In order to be able to recharge the individual capacitors to component voltages independent of their capacitance ratio, the charging circuit preferably includes means for recharging the individual capacitors to different prescribed voltages.

In another embodiment of the defibrillator/cardioverter according to the invention, a parameter memory is connected to the pulse generator in which are stored, for the different output pulses, different values of the pulse start, pulse duration and/or pulse height. The parameter memory is connected to a telemetry device for transmitting the values from a programming device into the parameter memory. It is thereby possible, in particular in the case of implantable devices, for the parameter values determining the current distribution in the case of a defibrillation to be transmitted from an external programming device into the implantable device.

Since the current distribution in the heart depends not only on the parameter values specified above, but also on the arrangement of the electrodes and the geometry of the heart, it is particularly advantageous to be able to determine in advance the influence of the electrode arrangement and the geometry of the heart on the current distribution. In a further embodiment of the invention, therefore, a measuring device for measuring the electrical impedance between the electrodes is provided. As an alternative, a measuring device can be provided for measuring an electric current in the current path of at least one output terminal of the pulse generator device, it then being possible for the pulse generator to transmit a measuring pulse to the heart and for a conclusion to be drawn, from the current thereby caused, about the electrode arrangement and the geometry of the heart.

Preferably, the measuring device with the telemetry device for transmitting the measured values is connected to the programming device. The measured values can then, for example, be graphically represented on a display device of the programming device and the operator can give advice for programming the parameter values (pulse start, pulse duration and pulse height) in order to achieve a desired current distribution in the heart.

In a further embodiment of the defibrillator/cardioverter according to the invention, the measuring device is connected at its output side via a control line to the means for automatically setting the pulse start, the pulse duration and/or the pulse height. In this way, the defibrillator automatically takes account of the respective arrangement of the electrodes and the geometry of the heart when determining the parameter values, so that a prescribed defined current distribution is achieved in the heart.

DESCRIPTION OF THE DRAWINGS

FIG. 1 is a block diagram of an exemplary embodiment of a defibrillator/cardioverter constructed in accordance with the principles of the present invention.

FIG. 2 shows an exemplary embodiment of the pulse generator shown in the block diagram according to FIG. 1.

FIG. 3 shows a diagram with the switching times of the controllable switches shown in FIG. 2.

FIGS. 4a to 4f show the current distribution obtained in the heart by means of the defibrillator according to FIGS. 1 and 2.

DESCRIPTION OF THE PREFERRED EMBODIMENTS

Figure 5:
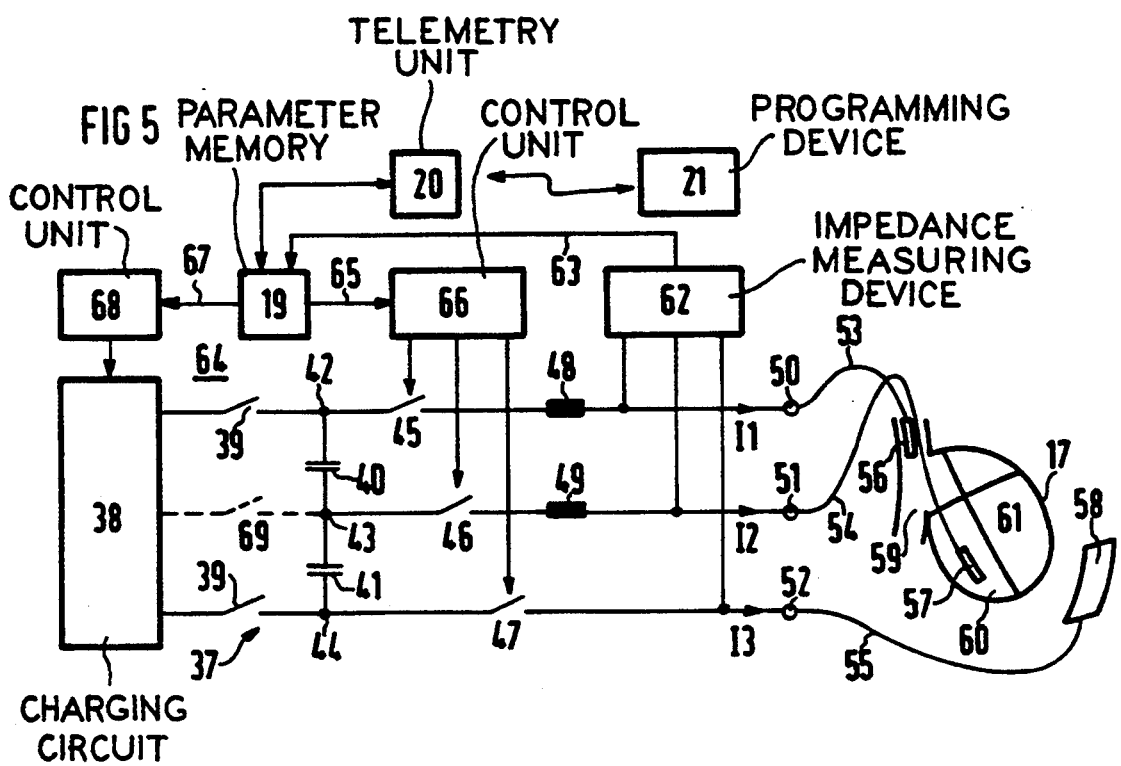
FIG. 5 is a block diagram of a further exemplary embodiment of the defibrillator/cardioverter constructed in accordance with the principles of the present invention.

In the block diagram shown in FIG. 1 of a defibrillator or cardioverter, a pulse generator for generating electric pulses is denoted by 1. The pulse generator 1 has three series-connected outputs 2, 3 and 4 having a total of four output terminals 5, 6, 7 and 8 which are connected via electrode lines 9, 10, 11 and 12 to four electrodes 13, 14, 15 and 16, which are arranged on a heart 17 represented in cross-section). The pulse generator 1 is connected via a control line 18 to a parameter memory 19 in which are stored respectively different values for the pulse start, the pulse duration and, possibly, the pulse height (amplitude) of the pulses generated by the pulse generator 1 at its outputs 2, 3 and 4. These values can be transmitted by means of a telemetry device 20 connected to the parameter memory 19 between the parameter memory 19 and a programming device 21. Such telemetric communication is advantageous particularly when the defibrillator shown in FIG. 1 is an implantable device; otherwise, the exemplary embodiment can be a non-implantable device. Consequently, the electrodes 13, 14, 15 and 16 can, as shown in FIG. 1, be arranged directly on the heart 17, or can be arranged individually inside the heart, subcutaneously, or outside on the patient's body. Furthermore, the number of electrodes used can be n (n>3)in general, the pulse generator 1 having n-1 outputs with n output terminals.

In order to defibrillate the heart 17, the pulse generator 1 generates at its outputs 2, 3 and 4 electrical voltage pulses U which, as indicated diagrammatically in FIG. 1, overlap temporally, a different number of pulses U being respectively simultaneously transmitted in directly successive time intervals T. This is achieved by performing the pulse transmission in accordance with the values, contained in the parameter memory 18, for the individual outputs 2, 3 and 4 with different times for the respective pulse start and the respective pulse duration. The influence this has on the defibrillation of the heart 17 is explained below with the aid of further exemplary embodiments.

FIG. 2 shows a particularly simple exemplary embodiment of the pulse generator 1, in which a capacitor 22 for recharging to a prescribed voltage can be connected to a charging circuit 25 via a switch arrangement 24 controlled by a control device 23. The capacitor 22 is connected on one side 26 to each one of the outputs 5 to 8 via four controllable switches 27 to 30, and on the other side 31 to each of the outputs 5 to 8 via four further controllable switches 32 to 35. The switches 27 to 30 and 32 to 35 can be turned on and off independently of one another by the control device 23. As shown in FIG. 1, four electrodes are connected to the output terminals 5 to 8.

An example of the control of the switches 27 to 30 and 32 to 35 during unbroken, directly successive time intervals A to F is represented in a diagram in FIG. 3. FIGS. 4a–4f schematically show the current distribution 36 resulting therefrom between the electrodes 13, 14, 15 and 16 during the individual time intervals A–F.

As shown in FIGS. 4a–4f for the different time intervals A to F, the current distribution 36 can be distributed over different regions of the heart tissue 17 (indicated diagrammatically). In particular, as the combination of FIGS. 4a–4f shows, control of the current distribution 36 can be performed in such a way that the current distribution 36 sequentially penetrates adjacent regions of the heart tissue 17 in the successive time intervals A to F, so that, in a manner similar to a concentrated water jet which is guided continuously over the base of a fire, the different regions of the heart tissue 17 are sequentially defibrillated. In this case, it is possible by selecting the switching sequence for the controllable switches 27 to 30 and 32 to 35 to concentrate the defibrillation of the heart tissue 17 firstly on the region of the heart tissue 17 most strongly affected by the fibrillation, and subsequently to extend it to edge regions of the heart tissue 17, or inversely, beginning with the defibrillation of less affected regions of the heart tissue 17, then moving to the most strongly affected region of the heart tissue 17. This process can also be repeated as frequently as required. It is thereby achieved that the individual regions of the heart tissue 17 are sequentially defibrillated and a resurgence of fibrillation in these regions is prevented.

In the exemplary embodiment shown in FIG. 5 of an implantable defibrillator 37, a charging circuit 38 can be switched via a controllable switch arrangement 39 to two series-connected capacitors 40 and 41. The series circuit of the capacitors 40 and 41 has three different terminals 42, 43 and 44 which are respectively connected to output terminals 50, 51 and 52 of the defibrillator 37 via switches 45, 46 and 47, which can be controlled independently of one another, as well as, in the case of terminals 42 and 43, via inductors 48 and 49. In accordance with the number of the series-connected capacitors 40 and 41, the output terminals 50, 51 and 52 form two series-connected outputs of the defibrillator 37 which are connected via electrode lines 53, 54 and 55 to electrodes 56, 57 and 58. In this case, the electrode 56 is arranged in the vena cava 59, the electrode 57 in the right ventricle 60, and the electrode 58 arranged opposite, preferably subcutaneously, the left ventricle 61 of the heart 17. An impedance measuring device 62 connected to the output terminals 50, 51 and 52 which measures the electrical impedance of the heart tissue 17 between the electrodes 56, 57 and 58 at prescribed instances, preferably directly before triggering the defibrillation of the heart 17. The impedance measuring signal evaluated in the measuring device 62 is fed via a control line 63 to a setting device 64 for automatically setting the respective pulse start, the pulse duration and the pulse height for the electric pulses to be transmitted to the heart 17 by the defibrillator 37. The setting device 64 includes a parameter memory 19 which is connected on the input side to the control line 63 and is connected via a first parameter output 65 to a control device 66 for individually turning on and off the switches 45, 46 and 47, and via a second parameter output 67 to a further control device 68 for setting the charging voltage generated by the charging circuit 38 for recharging the capacitors 40 and 41. The values contained in the parameter memory 19 for the pulse start, the pulse duration and the pulse height of the pulses to be generated can be transmitted by means of a telemetry device 20, connected to the parameter memory 19, to an external programming device 21 for informing an operator. In addition, the parameter values can also be entered by the operator into the parameter memory 19 via the programming device 21, or the operator can program boundary conditions under which automatic parameter setting is performed by the measuring device 62.

The charging circuit 38 generates a single charging voltage which, when the switch arrangement 39 is closed, is applied across the series-connected capacitors 40 and 41 and recharges them to component voltages dependent on the capacitances of the capacitors 40 and 41. As an alternative, the capacitors 40 and 41 can be recharged to component voltages independently of the ratio of their capacitance values, for which purpose the charging circuit 48 in each case delivers a charging voltage for each capacitor 40 and 41 and the two different charging voltages are switched via the controllable switch arrangement 38 extended by an additional switch 69 (represented by dashes) to the capacitors 40 and 41.

Thus, as long as the switch arrangement 39 is closed, the capacitors 40 and 41 are recharged to the charging voltage prescribed by the charging circuit 38, the component voltages across the individual capacitors 40 and 41 depending on their capacitance ratio or being set directly by the charging circuit 38. The different component voltages take into account the fact that the heart muscle mass is non-uniformly distributed with reference to the selected arrangement of the electrodes 56, 57 and 58. In order to defibrillate the heart 17, the switches 45, 46 and 47 are closed, so that the capacitors 40 and 41 are discharged via the inductors 48 and 49 and via the heart tissue 17 situated between the electrodes 56, 57 and 58, the heart 17 being fed different current pulses 11, 12 and 13 via the electrodes 56, 57 and 58. The steepness of the rising and falling edges of the current pulses 11, 12 and 13 is limited by the inductors 48 and 49, it being possible for the current pulses 11, 12 and 13 to take the form of strongly damped sinusoidal oscillations given appropriately high inductance values.

Apart from the geometry of the heart muscle and the arrangement of the electrodes 56, 57 and 58, the current distribution achieved in the heart 17 during defibrillation also depends on the selected component voltages across the capacitors 40 and 41 and the switching times for the switches 45, 46 and 47. In this case, the influence of the geometry of the heart 17 and of the arrangement of the electrodes 56, 57 and 58 on the current distribution before triggering defibrillation is determined by measuring the impedance between the electrodes 56, 57 and 58 and used to set the values for the component voltages at the capacitors 40 and 41 and the switching times for the switches 45, 46 and 47. As a result, a predetermined, defined distribution of the defibrillation current in the heart 17 is achieved.

Figure 6:
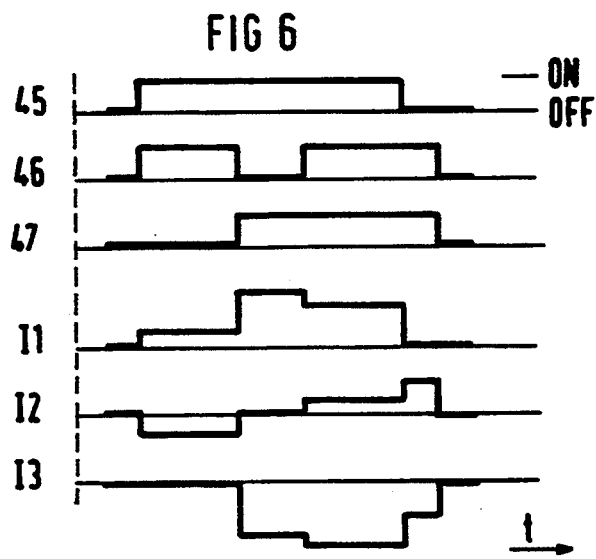
FIG. 6 shows the switching times for the controllable switches shown in FIG. 5 and the current characteristics resulting therefrom at the outputs of the defibrillator shown in FIG. 5.

An example of the control of the switches 45, 46 and 47 and the resultant characteristic of the currents 11, 12 and 13 are represented in a diagram in FIG. 6. In this case, a ratio of 1:2 was assumed for the component voltages across the capacitors 40 and 41. As FIG. 6 shows, because of the differently overlapping switching times for the switches 45, 46 and 47, it is possible to achieve different current characteristics 11, 12 and 13, even a precisely stepped bi-phasal characteristic in the case of the current 12. The current characteristics shown in FIG. 6 are to be understood only as one example for explaining the invention.

Figure 7:
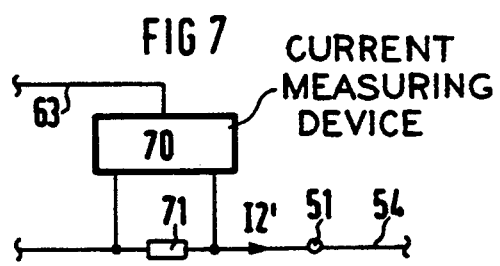
FIG. 7 shows an alternative exemplary embodiment of the measuring device present in the defibrillator according to FIG. 5.

FIG. 7 shows, as an alternative to the impedance measuring device 22 shown in FIG. 5, a measuring device 70 for recording a measuring current 12' in the electrode line 54, the measuring device 70 measuring the voltage drop caused in a measuring shunt 71 by the measuring current 12'. The measured value is used via the control line 63 to set the parameter values in the parameter memory 19. The current 12' is generated before defibrillation of the heart 17 by recharging the capacitors 40 and 41 via the charging circuit 38 to a charging voltage that is low by comparison with the voltages used for defibrillation purposes, and connecting them to the heart tissue 17 via the controllable switches 45 to 47 and the electrodes 56, 57 and 58.

Although modifications and changes may be suggested by those skilled in the art, it is the intention of the inventor to embody within the patent warranted hereon all changes and modifications as reasonably and properly come within the scope of his contribution to the art.

I claim as my invention:

1. A defibrillator/cardioverter comprising:
    a plurality of n electrodes, n being greater than or equal to three, adapted for delivering electrical pulses to the heart of a patient; and
    pulse generator means, having n-1 series-connected outputs with n output terminals respectively connected to said n electrodes, for generating an electrical output pulse at each of said outputs with a different plurality m of said output pulses being transmitted with temporal overlap to said heart via said electrodes in directly successive time intervals, with m greater than or equal to one and less than or equal to n-1.

2. A defibrillator/cardioverter as claimed in claim 1 wherein each of said output pulses has a pulse start, a pulse duration and a pulse height, and wherein said pulse generator means includes means for varying at least one of the pulse start, pulse duration and pulse height of said output pulses.

3. A defibrillator/cardioverter as claimed in claim 2 wherein said means for varying comprises:
    a capacitor connected across a charging circuit for charging said capacitor;
    a first set of controllable switches connected between one side of said capacitor and each of said output terminals;
    a second set of controllable switches connected between an opposite side of said capacitor and each of said output terminals; and
    control means for individually actuating each of said switches in said first and second sets of controllable switches for varying at least one of said pulse start, pulse duration and pulse height.

4. A defibrillator/cardioverter as claimed in claim 2 wherein said means for varying comprises:
    a charging circuit;
    n-1 series-connected capacitors connected across said charging circuit for charging said capacitors;
    a plurality of individually controllable switches respectively connected between said capacitors and said output terminals; and
    means for controlling said switches for varying at least one of said pulse start, pulse duration and pulse height.

5. A defibrillator/cardioverter as claimed in claim 4 wherein said charging circuit includes means for charging said capacitors individually to different voltages.

6. A defibrillator/cardioverter as claimed in claim 2 further comprising:
    a parameter memory, in which a plurality of different values of said pulse start, pulse duration and pulse height are stored for said output pulses and connected to said means for varying for transmitting said values to said means for varying for use in varying at least one of said pulse start, pulse duration and pulse height; and
    telemetry means for telemetrically communicating with said parameter memory for entering said different values into said parameter memory.

7. A defibrillator/cardioverter as claimed in claim 2 further comprising measuring means for measuring electrical impedance between said electrodes and for supplying a signal corresponding to said electrical impedance to said means for varying for automatically varying at least one of said pulse start, pulse duration and pulse height dependent on said electrical impedance.

8. A defibrillator/cardioverter as claimed in claim 2 further comprising measuring means for measuring electric current in a current path formed by at least one output terminal of said pulse generator means and for supplying an electrical signal corresponding to said electric current to said means for varying for automatically varying at least one of said pulse start, pulse duration and pulse height dependent on said electric current.

9. A defibrillator/cardioverter as claimed in claim 2 further comprising:
    means for measuring electrical impedance between said electrodes; and
    means for telemetrically communicating with said means for measuring and with said means for varying for providing an indication of said electrical impedance at a remote location and for permitting human intervention, based on said indication, to vary at least one of said pulse start, pulse duration and pulse height telemetrically.

10. A defibrillator/cardioverter as claimed in claim 2 further comprising:
    means for measuring electric current in a current path of at least one output terminal of said pulse generator means; and
    means for telemetrically communicating with said means for measuring and with said means for varying for providing an indication of said electric current at a remote location and for permitting human intervention, based on said indication, to vary at least one of said pulse start, pulse duration and pulse height telemetrically.

* * * * *